(12) United States Patent
Johnson et al.

(10) Patent No.: US 8,592,624 B2
(45) Date of Patent: Nov. 26, 2013

(54) PRODUCTION OF ETHYLENICALLY UNSATURATED ACIDS OR ESTERS THEREOF

(75) Inventors: David William Johnson, Redcar (GB); Trevor Huw Morris, Redcar (GB)

(73) Assignee: Lucite International UK Limited (GB)

( * ) Notice: Subject to any disclaimer, the term of this patent is extended or adjusted under 35 U.S.C. 154(b) by 329 days.

(21) Appl. No.: 12/992,906

(22) PCT Filed: May 15, 2009

(86) PCT No.: PCT/GB2009/050523
§ 371 (c)(1),
(2), (4) Date: Nov. 16, 2010

(87) PCT Pub. No.: WO2009/141641
PCT Pub. Date: Nov. 26, 2009

(65) Prior Publication Data
US 2011/0071311 A1    Mar. 24, 2011

(30) Foreign Application Priority Data

May 22, 2008   (GB) .................................. 0809332.0

(51) Int. Cl.
| C07C 51/50 | (2006.01) |
| C07C 69/54 | (2006.01) |
| C07C 67/62 | (2006.01) |
| C07C 57/03 | (2006.01) |
| C07C 57/04 | (2006.01) |
| C07C 69/533 | (2006.01) |

(52) U.S. Cl.
USPC ........... 560/214; 560/211; 560/218; 562/599; 562/600

(58) Field of Classification Search
None
See application file for complete search history.

(56) References Cited

U.S. PATENT DOCUMENTS

| 2,105,284 A | 1/1938 | Groll et al. |
| 6,544,924 B1 | 4/2003 | Jackson et al. |
| 6,670,501 B1 | 12/2003 | Harrison et al. |
| 2002/0165420 A1 | 11/2002 | Elomari et al. |
| 2003/0233012 A1 | 12/2003 | Jackson et al. |

FOREIGN PATENT DOCUMENTS

| DE | 44 30 086 A1 | 2/1996 |
| DE | 4430086 A1 | 2/1996 |
| JP | H06-48977 | 2/1994 |
| JP | H09-316022 | 12/1997 |
| JP | 2001-288147 | 10/2001 |
| JP | A-2001-288146 | 10/2001 |
| JP | 2007-055948 | 3/2007 |
| WO | WO 86/00236 A1 | 1/1986 |
| WO | WO 99/02481 A1 | 1/1999 |
| WO | WO 99/26915 A1 | 6/1999 |
| WO | WO 99/52628 A1 | 10/1999 |
| WO | WO 02/18138 A1 | 3/2002 |

OTHER PUBLICATIONS

Nov. 22, 2010 Written Opinion issued in Patent Application PCT/GB2009/050523.
Russian Official Action for Russian Application No. 2010152353/4(075714) dated Dec. 21, 2010.
Bruce A. Marien: "Stabilization of High Nitrile Polymers. I. Effect of Dienohilic Compounds" Journal of Polymer Science: Polymer Chemistry Edition, vol. 17, 1979, pp. 425-433, XP002551939 the whole document.
International Search Report mailed by European Patent Office on Nov. 6, 2009 for International Patent Application No. PCT/GB2009/050523.
English translation of Japanese Office Action dated Aug. 27, 2013 for Japanese Patent Application No. 2011-510048.

*Primary Examiner* — Yevegeny Valenrod
(74) *Attorney, Agent, or Firm* — Shumaker, Loop & Kendrick, LLP

(57) ABSTRACT

A production process for the manufacture of ethylenically unsaturated acids or esters thereof is described. The process includes the steps of reaction of an alkanoic acid, or ester of an alkanoic acid, of the formula $R^3$—$CH_2$—$COOR4$ where $R^3$ and $R^4$ are each independently hydrogen or an alkyl group, in the presence of a catalyst system to produce an ethylenically unsaturated acid or ester product. The process is characterised in that the acid or ester product is subsequently contacted with a dienophile to thereby remove discolouration therefrom. An ethylenically unsaturated acid or ester crude product purification process is also described.

13 Claims, 2 Drawing Sheets

PRODUCTION OF ETHYLENICALLY UNSATURATED ACIDS OR ESTERS THEREOF

This invention relates to the production of ethylenically unsaturated acids or esters thereof, particularly alkacrylic acids or alkyl (alk)acrylates such as methacrylic acid or alkyl (meth)acrylates and, in particular, purification of the said acid or ester product during such production.

Such acids or esters may be made by reacting an alkanoic acid (or ester) of the formula $R^3$—$CH_2$—$COOR^4$, where $R^3$ and $R^4$ are each, independently, a suitable substituent known in the art of acrylic compounds such as hydrogen or an alkyl group, especially a lower alkyl group containing, for example, 1-4 carbon atoms, with a suitable methylene source, for example, a source of formaldehyde. Thus, for instance, methacrylic acid or alkyl esters thereof, especially methyl methacrylate, may be made by the catalytic reaction of propionic acid, or the corresponding alkyl ester, e.g. methyl propionate, with formaldehyde as a methylene source in accordance with the reaction sequence 1.

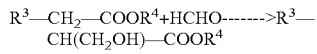

and

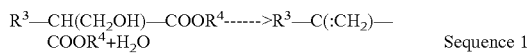   Sequence 1

An example of reaction sequence 1 is reaction sequence 2

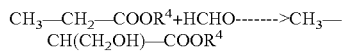

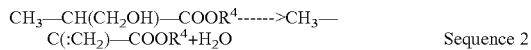   Sequence 2

The reaction is typically effected at an elevated temperature, usually in the range 250-400° C., using a basic catalyst. Where the desired product is an ester, the reaction is preferably effected in the presence of the relevant alcohol in order to minimise the formation of the corresponding acid through hydrolysis of the ester. Also for convenience it is often desirable to introduce the formaldehyde in the form of formalin. Hence, for the production of methyl methacrylate, the reaction mixture fed to the catalyst will generally consist of methyl propionate, methanol, formaldehyde and water.

Conventionally, methyl methacrylate has been produced industrially via the so-called acetone-cyanohydrin route. The process is capital intensive and produces methyl methacrylate at a relatively high cost.

The MMA product stream from the acetone-cyanohydrin route has an undesirable yellow hue and other impurities. However, these can be successfully removed by diamino or polyamino compounds such as N,N-diethylene triamine (DETA) or ortho-phenylenediamine. A new improved commercial process for the production of MMA uses a catalysed reaction between methylpropionate and formaldehyde as mentioned above. Unfortunately, this process also produces a yellow hue. Use of DETA alone to remove the yellow hue was surprisingly found to be unsuccessful.

According to a first aspect of the present invention there is provided a production process for the manufacture of ethylenically unsaturated acids or esters thereof, by reaction of an alkanoic acid, or ester of an alkanoic acid, of the formula $R^3$—$CH_2$—$COOR^4$ where $R^3$ and $R^4$ are each independently hydrogen or an alkyl group, in the presence of a catalyst system to produce said ethylenically unsaturated acid or ester product characterised in that the acid or ester product is subsequently contacted with a dienophile to thereby remove discolouration therefrom.

Preferably, the dienophile is a compound of formula I

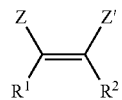

wherein Z is selected from the group consisting of —C(O)Y, —CN, —$NO_2$ or halo, wherein Y is selected from the group consisting of hydrogen, alkyl, hetero, —OR, halo or aryl, wherein R, $R^1$ and $R^2$ independently represent hydrogen, alkyl or aryl and hetero represents N, S or O which hetero atoms may be unsubstituted or substituted with one or more of the groups consisting of hydrogen, alkyl, —OR, aryl, aralkyl or alkaryl, wherein R is as defined for Y above; Z' may be any one of the groups selected for Z above or may additionally be hydrogen, alkyl, aryl or hetero; or Z and $Z^1$ may together be —C(O)Y(O)C— so that the dienophile forms a cyclic group of formula Ia

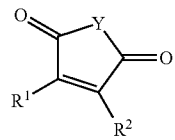

wherein $R^1$ and $R^2$ are as defined above, Y is hetero as defined above or Y represents an alkylene group of formula —$(CH_2)_s$— wherein S is 1, 2 or 3, preferably 1.

The reaction of the present invention may be a batch or continuous reaction and the subsequent contact with the dienophile may take place before and/or after other subsequent treatment steps. Typically, however, the crude product is substantially separated from the reactants before being brought into contact with the dienophile. In a continuous process of the present invention, the product may be present in a product stream which is contacted with the dienophile after reaction in a suitable reaction vessel according to the first aspect has been effected.

The process of the invention is particularly suitable in the manufacture of ($C_{0-8}$alk)acrylic acid or alkyl ($C_{0-8}$alk)acrylates, preferably methacrylic acid or especially methyl methacrylate, in which cases the alkanoic acid or ester is propionic acid or methyl propionate respectively. In particular, the process is particularly suitable for the reaction of an alkanoic acid or ester thereof with a methylene or ethylene source, such as a source of formaldehyde in the presence of a catalyst system.

The term "alkyl" when used herein, means, unless otherwise specified, $C_1$ to $C_{10}$ alkyl and includes methyl, ethyl, ethenyl, propyl, propenyl butyl, butenyl, pentyl, pentenyl, hexyl, hexenyl and heptyl groups, preferably, methyl, ethyl, propyl, butyl, pentyl and hexyl. Unless otherwise specified, alkyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, —$OR^{19}$, —$OC(O)R^{20}$, —$C(O)R^{21}$, —$C(O)OR^{22}$, —$NR^{23}R^{24}$, —$C(O)NR^{25}R^{26}$, —$SR^{28}$, —$C(O)SR^{30}$, —$C(S)NR^{27}R^{28}$, unsubstituted or substituted aryl, or unsubstituted or substituted Het, wherein $R^{19}$ to $R^{30}$ each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilicon groups, or mixtures thereof. Preferably, the alkyl groups are unsubstituted, preferably, linear and preferably, saturated.

The term "alk" or the like should, in the absence of information to the contrary, be taken to be in accordance with the above definition of "alkyl" except "$C_0$ alk" means non-substituted with an alkyl.

The term "aryl" when used herein includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The terms "alkaryl" or "aralkyl" should be construed with reference to the definitions of the "alkyl" and "aryl" parts above.

The term "halo" when used herein means a chloro, bromo, iodo or fluoro group, preferably, chloro or fluoro. Without prejudice to the scope of protection and without being bound by theory, upon making this surprising discovery, the inventors tested whether there may be a diene impurity that was causing the colouration. However, reaction with the dienophile does not seem to affect the diene impurities identified, indicating that the impurity may not be a diene.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

Preferably, $R^1$ and $R^2$ are independently selected from hydrogen or alkyl. Preferably, when $R^1$ and/or $R^2$ are alkyl they are selected from $C_1$-$C_4$ alkyl, wherein alkyl is otherwise defined above, more preferably, methyl or ethyl, most preferably, when alkyl, they are methyl. Typically, when one of $R^1$ or $R^2$ is alkyl, the other is hydrogen, more typically, one is hydrogen and the other is methyl or ethyl, most typically, one is hydrogen and the other is methyl. In especially preferred embodiments, both $R^1$ and $R^2$ are hydrogen.

Optionally, the crude product is also treated with DETA. The treatment with DETA has the benefit of removing other impurities from the crude product. Preferably, the treatment of the crude product with DETA takes place in a separate step than the treatment with the dienophile. Surprisingly, it has been found that the dienophile of the invention is more effective when not in the presence of DETA than when it is present and there may be a reaction between the respective compounds.

Advantageously, despite the reactivity of DETA with dienophiles, dienophiles act as a beneficial agent for removal of colour from a product produced by the above process, particularly in the absence of DETA. Accordingly, DETA treatment and the treatment of the present invention should preferably, take place in separate steps to avoid reaction therebetween. Preferably, the DETA treatment of the crude product follows the dienophile treatment step.

Preferably, the DETA and/or dienophile compound concentrations are selected so that a suitable excess is present for their respective uses. DETA has a relatively low reactivity and excess (compared to impurity concentration) must be present to effect reaction with any impurities. On the other hand, dienophile compounds of the present invention are susceptible to hydrolysis or alcoholysis forming acids and esters readily, accordingly, a large excess (compared to the potential colour former concentration) is present to effect removal of the relevant colour former. Typically, the dienophile is present in the range 10 to 50,000 ppm by weight in the crude product to be treated, more preferably, 100 to 20,000 ppm by weight in the crude product to be treated, most preferably, 1000 to 10,000 ppm by weight in the crude product to be treated. However, the concentration of the dienophile is not limited and depends on the concentration of impurity to be removed. Typically, in a continuous process, the crude product to be treated is a product stream.

By impurities is meant products of the reaction other than ethylenically unsaturated acids or esters but not reactants or catalyst.

Suitable dienophiles in accordance with the present invention may be selected from the list comprising or consisting of:— maleic anhydride, maleimide, thiophen-2,5-dione, acrylic acid, acrolein, alkyl acrylates, acrylonitrile, maleic acid, dialkyl maleate and vinyl halides. Preferred dienophiles are maleic anhydride, maleimide and thiophene-2,5-dione, more preferably, maleic anhydride and maleimide, most preferably, maleic anhydride.

According to a second aspect of the present invention there is provided an ethylenically unsaturated acid or ester crude product purification process characterised in that the acid or ester crude product is contacted with a dienophile to remove at least one colour forming impurity, preferably, yellow colour forming impurity, therefrom.

A suitable process for preparing the ethylenically unsaturated acids or ester prior to purification by contact with a dienophile comprises contacting an alkanoic acid or ester of the formula $R^3$—$CH_2$—$COOR^4$, with a suitable source of methylene or ethylene of formula as defined below:

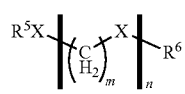

I where $R^5$ and $R^6$ are independently selected from $C_1$-$C_{12}$ hydrocarbons, preferably, $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H;

X is either O or S, preferably, O;

n is an integer from 1 to 100, preferably 1 to 10, more preferably 1 to 5, especially, 1-3;

and m is 1 or 2, preferably 1;

in the presence of a suitable catalyst, and optionally in the presence of an alcohol; wherein $R^3$ and $R^4$ are each independently hydrogen or an alkyl group.

In a particularly preferred embodiment the compound of formula I is derived from formaldehyde the presence of methanol and/or water. In such a case, the compound of formula I may be defined as a suitable source of formaldehyde.

For the avoidance of doubt, a suitable source of formaldehyde includes any equilibrium composition which may provide a source of formaldehyde. Examples of such include but are not restricted to methylal (1,1 dimethoxymethane), polyoxymethylenes —$(CH_2$—$O)_i$— wherein i=1 to 100 formalin (formaldehyde, methanol, water) and other equilibrium compositions such as a mixture of formaldehyde, methanol and methyl propionate.

Typically, the polyoxymethylenes are higher formals of formaldehyde and methanol $CH_3$—O—$(CH_2$—$O)_i$—$CH_3$ ("formal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—$(CH2$-$O$—$)_iR^{32}$, where $R^{31}$ and $R^{32}$ may be the same or different groups and at least one is selected from a $C_2$-$C_{10}$ alkyl group, for instance $R^{31}$=isobutyl and $R^{32}$=methyl.

Preferably, the suitable source of formaldehyde is selected from 1,1 dimethoxymethane, higher formals of formaldehyde and methanol, $CH_3$—O—$(CH_2$—$O)_i$—$CH_3$ where i=2, formalin or a mixture comprising formaldehyde, methanol and methyl propionate.

Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol:water in the ratio 30 to 60%:0.03 to 20%:35 to 60% by weight. Most preferably, by the term formalin is meant a mixture of formaldehyde:methanol:water in the ratio 35 to 55%:0.05 to 18%: 42 to 53% by weight.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

Therefore, according to a still further aspect of the present invention there is provided a process for preparing and purifying an ethylenically unsaturated acid or ester of the following formula:—

wherein $R^3$ and $R^4$ are defined in the same way as for the alkanoic acid or ester above; and m is 1 or 2;

the process comprising the stems of— a) contacting an alkanoic acid or ester of the formula $R^3$—$CH_2$—$COOR^4$, wherein $R^3$ and $R^4$ are as already defined above, with a methylene or ethylene source of formula I, in the presence of a suitable catalyst and optionally in the presence of an alcohol to produce an impure ethylenically unsaturated acid or ester of the formula:—

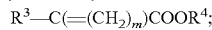

b) subsequently contacting the impure ethylenically unsaturated acid or ester of step (a) with a dienophile to thereby remove discolouration therefrom.

Preferably, the ethylenically unsaturated acid or ester is selected from methacrylic acid, acrylic acid, methyl methacrylate, ethyl acrylate or butyl acrylate, more preferably, it is an ethylenically unsaturated ester, most preferably, methyl methacrylate.

The process is particularly suitable for the purification of $(C_{0-8}alk)$acrylic acid or alkyl $(C_{0-8}alk)$acrylates, typically from the reaction of the corresponding alkanoic acid or ester thereof with a methylene or ethylene source such as formaldehyde in the presence of a catalyst system, preferably methacrylic acid or especially methyl methacrylate (MMA) from propanoic acid or methyl propionate respectively.

Accordingly, a typical source for an MMA crude product is the catalytic conversion of methyl propionate (MEP) to MMA using formaldehyde. A suitable catalyst for this and generally in the invention is a caesium catalyst on a support, for instance, silica which may include other metals and metal compounds.

Preferably, the amount of dienophile contacted with the product in the present invention is between 100 and 50,000 ppm by weight crude product, more preferably, between 500 and 20,000 ppm by weight crude product, most preferably between 1000 and 10,000 ppm by weight crude product.

As the product is not pure prior to addition of the dienophile, the optimal ppm concentration may need to be initially determined retrospectively after determining product levels and the effectiveness of subsequent colour removal from the crude product.

In the present invention, it is possible that other colour forming impurities are present during the reaction with the dienophile which are themselves subsequently removed in further steps. Therefore, the effectiveness of the colour removal by the dienophile may be determined after these further treatment steps.

Typical conditions of temperature and pressure in the crude product for addition of dienophile are between 50° C. and 200° C., more preferably, 80° C. and 150° C., most preferably, 90° C. and 130° C.; between 0.001 MPa and 1 MPa, more preferably, 0.003 MPa and 0.5 MPa, most preferably, between 0.01 MPa and 0.2 MPa.

The yellow hue or discolouration which is removed by the process of the present invention can be removed from both impure and relatively pure crude product. If it is removed from relatively impure crude product, then the colour after treatment may appear little changed because of the presence of other coloured impurities which are readily removed in the normal purification process. In such cases, the improvement in colour can be observed after further purification steps. Typically, an impure crude product of the present invention has a purity prior to the dienophile treatment step of at least 60% w/w $(C_{0-8}alk)$ acrylic acid or alkyl $(C_{0-8}alk)$acrylate/ crude product, more typically at least 70% w/w, most typically, at least 80% w/w. The process of the present invention is found to be particularly advantageous in such product streams Alternatively, relatively high purity product streams can be treated in which case the improvement in colour can be observed directly after treatment and also after separation of the purified $(C_{0-8}alk)$acrylic acid or alkyl $(C_{0-8}alk)$ acrylate from the unreacted dienophile, degradation products from decolouration reaction, and other impurities which may be separated by distillation. In this case the crude product of the present invention has a purity prior to the dienophile treatment step of at least 90% w/w $(C_{0-8}alk)$acrylic acid or alkyl $(C_{0-8}alk)$acrylate/crude product, more typically at least 95% w/w, most typically, at least 97% w/w.

Embodiments of the invention will now be described with reference to the following non-limiting examples and with reference to the figures and by way of illustration only.

COMPARATIVE TESTS

Figure 1:
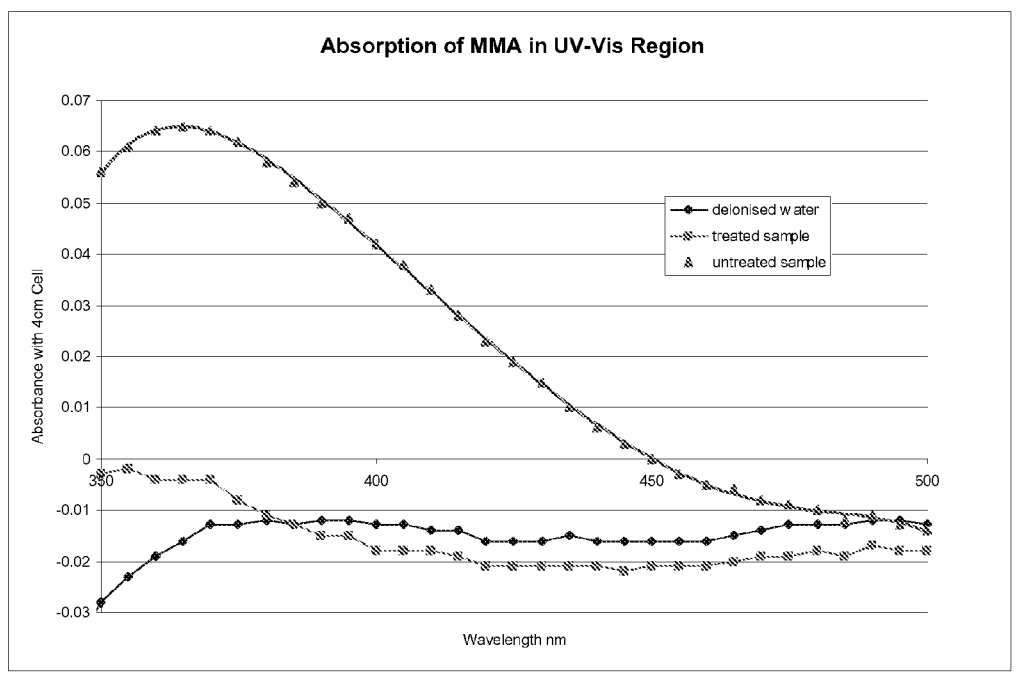
FIG. 1 shows UV-visible spectra for samples treated according to the invention.

Various comparative tests were performed to examine removal of colour from an MMA crude product.

Comparative Oxygen Treatment

A study was made to determine whether formation or degradation of colour was promoted by oxygen.

Samples of MMA were heated at different temperatures and times with air or nitrogen bubbling through the MMA rich solutions in flasks with condensers to prevent distillation. There was no difference in the colour of the air and the nitrogen treated samples. Accordingly, oxygen treatment was found ineffective.

Time and Light Stability of Colour

The colour is not indefinitely stable. A sample of MMA was examined for Hazen value (also known as the Platinum-Cobalt/APHA Colour defined in ASTM D 1209, for clear, light yellow liquids, defined by specified dilutions of a platinum-cobalt stock solution, ranging from 0 at the light end of the scale to 500 at the darkest) immediately after sampling. Samples were stored in darkness in two locations. Samples of each were retested after 30 days. The colour testing was as follows:

TABLE 1

|  | Hazen Value |
| --- | --- |
| Fresh Sample | 23 |
| Location 1 (after 30 days) | 6 |
| Location 2 (after 30 days) | 13 |

Comparative Heat Removal

Heat stability was examined further with respect to heating samples of MMA for 75 min and 315 min under total reflux (103° C.). The Hazen readings are:

TABLE 2

| Minutes Heating | Hazen Value |
| --- | --- |
| 0 | 23 |
| 75 | 12 |
| 315 | 48 |

Thus the colour initially fell and then rose again with heat treatment. It is suspected that this rise was due to formation of MMA oligomers, some of which are weakly coloured. Accordingly, heating is unsuitable for colour removal, although mild heating for short periods may reduce colour.

Comparative Absorption Systems

A number of adsorption materials were compared for colour removal.

1 Charcoal

Several forms of decolourising charcoal were used. After leaving at room temperature overnight with approx 1 g carbon per 50 ml of MMA, the MMA was separated by filtration through micron filters. There was no benefit in colour removal.

TABLE 3

| Material | Hazen Value |
| --- | --- |
| MMA | 23 |
| Sample + Decolourising Charcoal Ex Aldrich | 28 |
| Sample + DARCO G60 Charcoal | 33 |

2 Sodium Borohydride

Sodium borohydride was added to samples of the MMA (ca 2 g/50 ml MMA). There was no observable reaction. The samples were then treated as shown in the table:

TABLE 4

| Sample | Hazen Value |
| --- | --- |
| Fresh Sample | 23 |
| 90 min reflux at 103° C. | 16 |
| 90 min at 60° C. | 24 |

The colour levels appear similar to that which could have been expected from equivalent beatings in the absence of borohydride. Therefore, there is no evidence that sodium borohydride is having an impact on colour.

3 Acidic and Basic Columns

The following materials, all available from Aldrich Fine Chemicals, were used for adsorption measurements:

Aluminum Oxide Acidic
" " Basic
" " Neutral
" " Typ 506-C-1

Silica gel 70-230 mesh 60A For column chromatography
" " 60-200 mesh Typ 22
" " 35-70 mesh 40A Typ 10181

50 ml samples of each material were packed into a 100 ml column.

TABLE 5

|  | Hazen Value |
| --- | --- |
| Untreated MMA | 6 |
| Silica gel Typ22, 60-200mesh | 6 |
| Silica gel 70-230mesh 60A | 6 |
| Silica gel Typ 10181, 35-70mesh 40A | 6 |
| Silica gel Typ 506-C-1 | 6 |
| Aluminium oxide Basic | 8 |
| Aluminium oxide Neutral | 6 |
| Aluminium oxide Acidic | 3 |

The MMA treated with the acidic aluminum oxide fell to 3 Hazen units (from the starting figure of 6 units). None of the other samples was affected, indeed the basic alumina gave a slightly higher level of colour.

A second series of experiments was performed with the acidic alumina to examine the capacity of the 10 ml column to remove colour.

TABLE 6

|  | Hazen Value |
| --- | --- |
| Untreated MMA | 6 |
| first 50 ml eluate | 3 |
| second 50 ml eluate | 4 |
| third 50 ml eluate | 5 |
| fourth 50 ml eluate | 5 |
| fifth 50 ml eluate | 6 |
| sixth 50 ml eluate | 6 |

Thus the capacity of the column is very low and this does not appear to present a suitable method for colour removal.

Reaction with Various Compounds

The evidence of removal of colour with time, and the apparent absence of impact of oxygen suggests that the coloured material may be fairly unreactive. Nevertheless, the reaction with some dienophile compounds was examined.

Two series of samples are presented in Table 7 and 8. In each case, the sample of MMA was heated for 30 minutes (at 80° C.) under reflux and then about 80% of the MMA was removed by low pressure distillation on a rotary evaporator. Due to the unpredictability of the colour level from sample to sample, the different untreated MMA samples may have different starting Hazen values.

TABLE 7

| Additive | Actual Hazen Value |
| --- | --- |
| No additive | 19 |
| Benzoquinone | 13 |
| Maleic anhydride | 7 |
| Dimethyl maleate | 10 |

TABLE 8

| Additive | Actual Hazen Value |
| --- | --- |
| MMA untreated | 28 |
| Naphthaquinone | 15 |
| Fumaronitrile | 25 |
| Maleimide | 9 |
| Benzoquinone | 13 |
| Acrylamide | 19 |
| Maleic Anhydride | 7 |

Surprisingly, the dienophiles are clearly more effective than other systems. Benzoquinone appears to have a positive impact as does naphthaquinone and fumaronitrile but maleimide and, particularly, maleic anhydride are particularly effective.

A further study was attempted using freshly prepared MMA with a Hazen value of about 35. 50 ml samples were tested in the same manner as above, at 80° C. for 30 minutes, followed by vacuum distillation on the rotary evaporator. 2 samples were tested; a control without additives and 3 wt % maleic anhydride.

In the case of the maleic anhydride, the distillate and residues were essentially colourless to the eye.

Reaction with Maleic Anhydride
Addition to MMA

The impact of maleic anhydride 2000 ppm was examined by heating a 500 ml batch of MMA for 30 min at 80° C., followed by removal of ca 80% of the contents of the flask overhead by rotary evaporation at reduced pressure. The colour of the distillate and residue was measured as shown below in Table 9.

TABLE 9

| | Actual Hazen Values |
| --- | --- |
| Starting MMA | 19 |
| After addition of MAH, Distillate | 5 |
| After addition of MAH, Residue | 9 |

The coloured MMA was studied using a UV-Visible spectrophotometer. FIG. 1 shows the UV-visible spectrum taken every 5 nm for samples of deionised water, a decolourised sample of MMA produced (according to the invention) and a coloured untreated sample. Each sample was taken in a 4 cm cell against deionised water as a reference.

An adsorption appears to peak at 360 nm. The peak is essentially not present in the treated sample.

The observed colour is due to an absorption in the UV tailing into the visible region of the UV-Visible spectrum. The absorption has disappeared by ca 500 nm.

Addition of Maleic Anhydride to a Pilot Plant Stream

Maleic anhydride was added to a pilot plant MMA production stream at 1000 ppm relative to the process stream. The level was increased in stages to over 7000 ppm.

Figure 2:
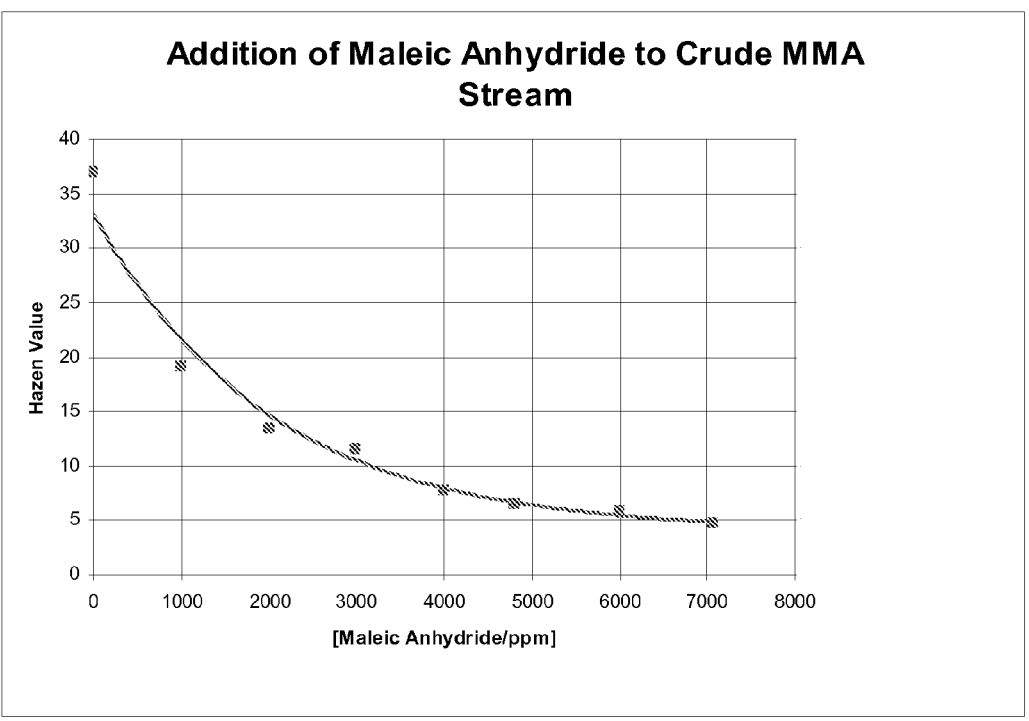
FIG. 2 shows hazen values of samples treated according to the invention.

The impact on the colour of the MMA derived following distillation of lights and heavies is shown in the FIG. 2. FIG. 2 shows the Impact of Maleic Anhydride on Pilot Plant MMA Product Stream when added to the product stream at a defined level relative to the flow from the column.

The data used in FIG. 2 are tabulated below (Table 10):

TABLE 10

| Fed MAH | Hazen Value |
| --- | --- |
| 0 | 37 |
| 1000 | 19.2 |
| 2000 | 13.5 |
| 2000 | 13.5 |
| 3000 | 11.5 |
| 4000 | 7.7 |
| 4000 | 7.7 |
| 4800 | 6.5 |
| 6000 | 5.9 |
| 7200 | 4.7 |
| 7200 | 4.7 |

The data were fitted to an exponential decay assuming a zero value for the Hazen scale of 4 units.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A production process for the manufacture of ethylenically unsaturated acids or esters thereof, by reaction of an alkanoic acid, or ester of an alkanoic acid, of the formula $R^3$—$CH_2$—$COOR^4$ where $R^3$ and $R^4$ are each independently hydrogen or an alkyl group, in the presence of a catalyst system to produce said ethylenically unsaturated acid or ester product characterised in that the acid or ester product is subsequently contacted with a dienophile to thereby remove discolouration therefrom; wherein the dienophile is different from said ethylenically unsaturated ester or acid product.

2. A production process according to claim 1, wherein the dienophile is a compound of formula I

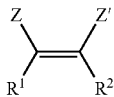
I wherein Z is selected from the group consisting of —C(O)Y, —CN, —NO$_2$ or halo, wherein Y is selected from the group consisting of hydrogen, alkyl, hetero, —OR, halo or aryl, wherein R, R$^1$ and R$^2$ independently represent hydrogen, alkyl or aryl and hetero represents N, S or O which hetero atoms may be unsubstituted or substituted with one or more of the groups consisting of hydrogen, alkyl, —OR, aryl, aralkyl or alkaryl, wherein R is as defined for Y above; Z' may be any one of the groups selected for Z above or may additionally be hydrogen, alkyl, aryl or hetero; or Z and Z' may together be —C(O)Y(O)C— so that the dienophile forms a cyclic group of formula Ia

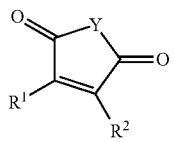
Ia wherein R$^1$ and R$^2$ are as defined above, Y is hetero as defined above or Y represents an alkylene group of formula —(CH$_2$)$_S$— wherein S is 1, 2 or 3.

3. A production process according to claim 1, wherein the ethylenically unsaturated acids or esters are selected from a C$_{0-8}$alk acrylic acid or alkyl (C$_{0-8}$alk)acrylate.

4. A production process according to claim 1, wherein the reaction is that of an alkanoic acid or ester thereof with a methylene or ethylene source such as a source of formaldehyde in the presence of the catalyst system.

5. A production process according to claim 2, wherein R$^1$ and R$^2$ are independently selected from hydrogen or alkyl.

6. A production process according to claim 2 wherein when one of R$^1$ or R$^2$ is alkyl, the other is hydrogen.

7. A production process according to claim 2, wherein both R$^1$ and R$^2$ are hydrogen.

8. A production process according to claim 1, wherein DETA treatment of the acid or ester product also takes place in a separate step than contact with a dienophile.

9. A production process according to claim 8, wherein the dienophile concentration and, if present, the DETA concentration is selected so that a suitable excess is present for their respective uses.

10. A production process according to claim 1, wherein the dienophile is present in the range 10 to 50,000 ppm by weight in the crude product to be treated.

11. A production process according to claim 1, wherein the dienophile is selected from the list consisting of:—
maleic anhydride, maleimide, thiophen-2,5-dione, acrylic acid, acrolein, alkyl acrylates, acrylonitrile, maleic acid, dialkyl maleate and vinyl halides.

12. An ethylenically unsaturated acid or ester crude product purification process characterised in that the acid or ester crude product is contacted with a dienophile to remove at least one colour forming impurity therefrom.

13. A process for preparing and purifying an ethylenically unsaturated acid or ester of the following formula:—

wherein R$^3$ and R$^4$ are defined in the same way as for the alkanoic acid or ester above; and m is 1 or 2;
the process comprising the steps of—
a) contacting an alkanoic acid or ester of the formula R$^3$—CH$_2$—COOR$^4$, wherein R$^3$ and R$^4$ are as already defined above, with a methylene or ethylene source of formula I,

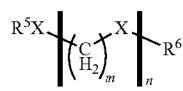
I where R$^5$ and R$^6$ are independently selected from C$_1$-C$_{12}$ hydrocarbons, preferably, C$_1$-C$_{12}$ alkyl, alkenyl or aryl as defined herein, or H, more preferably, C$_1$-C$_{10}$ alkyl, or H, most preferably, C$_1$-C$_6$ alkyl or H, especially, methyl or H;
X is either O or S, preferably, O;
n is an integer from 1 to 100, preferably, 1 to 10, more preferably 1 to 5, especially, 1-3;
and m is 1 or 2, preferably 1;
in the presence of a suitable catalyst and optionally in the presence of an alcohol to produce an impure ethylenically unsaturated acid or ester of the formula:—

b) subsequently contacting the impure ethylenically unsaturated acid or ester of step (a) with a dienophile to thereby remove discolouration therefrom; wherein the dienophile is different said ethylenically unsaturated ester or acid product.

* * * * *

UNITED STATES PATENT AND TRADEMARK OFFICE
CERTIFICATE OF CORRECTION

Page 1 of 1

| | |
|---|---|
| PATENT NO. | : 8,592,624 B2 |
| APPLICATION NO. | : 12/992906 |
| DATED | : November 26, 2013 |
| INVENTOR(S) | : David William Johnson et al. |

It is certified that error appears in the above-identified patent and that said Letters Patent is hereby corrected as shown below:

In the claims

In column 12, Line 53, add the word --from-- after the word different.

Signed and Sealed this
Eleventh Day of February, 2014

Michelle K. Lee
*Deputy Director of the United States Patent and Trademark Office*